United States Patent
Fuertes et al.

(10) Patent No.: US 7,342,050 B2
(45) Date of Patent: Mar. 11, 2008

(54) METHOD FOR PREPARING A LACTIC ACID ESTER COMPOSITION AND USE THEREOF AS SOLVENT

(75) Inventors: Patrick Fuertes, Lambersart (FR); Rodolphe Tamion, Allouagne (FR); Guy Fleche, Hazebrouck (FR); Serge Comini, La Gorgue (FR)

(73) Assignee: Roquette Freres, Lestrem (FR)

( * ) Notice: Subject to any disclaimer, the term of this patent is extended or adjusted under 35 U.S.C. 154(b) by 950 days.

(21) Appl. No.: 10/148,793

(22) PCT Filed: Dec. 26, 2000

(86) PCT No.: PCT/FR00/03685

§ 371 (c)(1),
(2), (4) Date: Jun. 4, 2002

(87) PCT Pub. No.: WO01/47860

PCT Pub. Date: Jul. 5, 2001

(65) Prior Publication Data

US 2003/0008927 A1 Jan. 9, 2003

(30) Foreign Application Priority Data

Dec. 28, 1999 (FR) .................... 99 16608

(51) Int. Cl.
*C08J 3/11* (2006.01)
*C08G 63/08* (2006.01)

(52) U.S. Cl. .................. 516/108; 516/98; 516/104; 528/176; 528/192

(58) Field of Classification Search ............. 516/98, 516/104, 108; 528/176, 192
See application file for complete search history.

(56) References Cited

U.S. PATENT DOCUMENTS

| 4,678,516 A | * | 7/1987 | Alderman et al. | 514/781 |
| 5,071,754 A | * | 12/1991 | Walkup et al. | 435/135 |
| 5,142,023 A | * | 8/1992 | Gruber et al. | 528/354 |
| 5,210,296 A | | 5/1993 | Cockrem et al. | |
| 5,252,473 A | * | 10/1993 | Walkup et al. | 435/135 |
| 5,264,617 A | | 11/1993 | Brake | |
| 5,420,304 A | * | 5/1995 | Verser et al. | 549/274 |
| 5,525,358 A | * | 6/1996 | Popp | 424/486 |
| 5,723,639 A | | 3/1998 | Datta et al. | |
| 5,750,732 A | * | 5/1998 | Verser et al. | 549/274 |
| 6,130,200 A | * | 10/2000 | Brodbeck et al. | 514/2 |
| 6,218,448 B1 | * | 4/2001 | Kraaijevanger et al. | 524/31 |
| 6,664,413 B1 | * | 12/2003 | Cockrem | 560/204 |

FOREIGN PATENT DOCUMENTS

| EP | 0 614 983 | | 9/1994 |
| EP | 0 628 533 | | 12/1994 |
| JP | 06065230 A | * | 3/1994 |
| JP | 08040983 A | * | 2/1996 |
| WO | WO 93/15127 | | 8/1993 |

OTHER PUBLICATIONS

XP-002146865 Derwent Publication of CN 1 229 790, Mar. 19, 1996.
Espacenet Abstract of JP 8-040983, Aug. 1, 1994.

* cited by examiner

*Primary Examiner*—Randy Gulakowski
*Assistant Examiner*—T. J. Kugel
(74) *Attorney, Agent, or Firm*—Young & Thompson

(57) ABSTRACT

The invention concerns a method for preparing a lactic acid ester composition based on a lactic acid composition involving a step of transforming the composition into a lactic acid oligomeric composition having a mean degree of polymerisation (DPM) ranging between 2 and 30 approximately; and a step which involves mixing and reacting said oligomeric composition with an alcohol, in the presence of a transesterification catalyst, to esterify all or part of the lactic acid contained in said oligomeric composition. The invention also concerns the use of ethyl lactate as solvent for preparing gelified compositions.

16 Claims, No Drawings

METHOD FOR PREPARING A LACTIC ACID ESTER COMPOSITION AND USE THEREOF AS SOLVENT

FIELD OF THE INVENTION

A subject matter of the present invention is a novel process for the preparation of a lactic acid ester composition from a lactic acid composition, it being possible for said process advantageously to be carried out continuously. The invention is also targeted at the use of the lactic acid ester composition thus obtained as solvent useful, inter alia, in the preparation of gelled compositions.

BACKGROUND OF THE INVENTION

The industrial use of solvents such as chlorinated solvents, glycols and glycol ethers is being increasingly called into question because of the toxicity of these products and their negative effect on the environment. There is therefore a search to substitute them by "green" solvents, namely biodegradable and nontoxic solvents, such as lactic acid esters and in particular ethyl lactate. The latter exhibits a number of physicochemical properties which allow it, at least potentially, to substitute for all or some of the conventional solvents and, inter alia:
- an excellent solvating power for resins (nitrocellulose, acrylic resins, polyurethanes, polyesters, alkyds, epoxy, and the like),
- a relatively high solubility in water and a generally good solubility in the majority of organic solvents,
- a relatively low volatility, allowing, for example, its effective use in surface treatment applications,
- a relatively high boiling point (154° C.), allowing its effective use in applications involving high temperatures.

The solvent properties of ethyl lactate and other lactic acid esters can advantageously be taken advantage of in numerous fields of activity, such as the metal industries, the automobile and aviation industries, the paint and ink industries, the resin and varnish industries, the pharmaceutical and cosmetological industries, and the semiconductor industries.

It should be specified that the notion of solvent is in this instance in no way limiting and includes, in particular, the notions of cosolvent, cleaning, degreasing or stripping agent.

These lactic acid esters, in particular ethyl lactate or butyl lactate, have, however, other industrial uses as synthetic intermediates, in particular in the preparation:
- of lactic acid of very high purity, as disclosed, for example, in U.S. Pat. No. 5,210,296 and EP 614 983, or,
- of lactide, i.e. of cyclic dimer of lactic acid, and then of polylactides, as disclosed for example, in patent WO 93/15127.

Despite its undeniable advantage as solvent or synthetic intermediate, a product such as ethyl lactate remains to this day a product which is still not manufactured and used industrially to any great extent, in particular with regard to chlorinated solvents, glycols or glycol ethers. This is because of its price which, by way of example, is currently still two to four times higher than that of the main commercially available glycol ethers.

It is widely known that the difficulty in preparing ethyl lactate industrially at an economically acceptable cost is related in particular to the twofold technical constraint 1) of having to continuously remove the water present in the reaction medium for the purposes of shifting the equilibrium of said reaction in the desired direction and 2) of having to employ amounts of alcohol, in this instance of ethanol, which are in large excess in comparison with those theoretically necessary for the reaction for the esterification of lactic acid.

This constraint is all the more pronounced because ethanol exhibits, in comparison with other alcohols, such as butanol, an azeotrope which is low in water, rendering the removal of the water necessarily expensive.

In fact, some technologies for the preparation of lactic acid esters are regarded as inapplicable to the specific production of ethyl lactate. This is the case, for example, with the processes exemplified in the abovementioned U.S. Pat. No. 5,210,296 and EP 614 983, disclosing the preparation of butyl lactate after employing n-butanol in a culture medium, optionally concentrated and/or purified, having generated ammonium lactate.

According to the authors of these patents, alcohols comprising 4 to 5 carbon atoms are those, among the alcohols which can be used for esterifying lactic acid, which exhibit the best overall economic compromise in terms of yields of formation and then of purification of esters but also of optional subsequent hydrolysis of said esters for the purpose of recovering lactic acid of high purity. n-Butanol is thus disclosed in U.S. Pat. No. 5,210,296 as exhibiting the following technical/economic advantages:
- boiling point (117.7° C.) very significantly greater than that of water and very significantly lower than that of butyl lactate (187° C.),
- low miscibility with water and possibility of forming heterogeneous azeotropes with water,
- possibility of being distilled without giving rise to problems a) of polymerization or dimerization of butyl lactate, b) of hydrolysis of butyl lactate and c) of increase in the viscosity of the reaction medium.

It has recently been envisaged, in U.S. Pat. No. 5,723,639, to improve the abovementioned processes for the preparation of lactic acid esters from ammonium lactate and in particular to be able to render said processes truly applicable to the preparation of ethyl lactate and/or to the use of limited reaction temperatures, i.e. lower than 100° C. Said patent claims, for this purpose, the necessary use of a stage of pervaporation of the esterification medium for the purpose of removing therefrom both water and ammonia, this being achieved without concomitant removal of the alcohol (ethanol, butanol) or of the ester formed (ethyl lactate or butyl lactate).

However, this technology requires the use of relatively specific and expensive pervaporation devices and in particular of pervaporation membranes which have to exhibit, but in particular to retain over time, very specific characteristics of selectivity and of resistance to the conditions of the medium (temperatures of between 75 and 150° C., presence of acidic or alkaline compounds, and the like).

In addition, while the possibility of operating at relatively low temperatures (80-95° C. for example) makes it possible to limit the level of ethanol employed to a value of 2 mol/mole of lactic acid, as described in example 6 and 7 of said patent, this possibility still in practice has a number of harmful effects on the general economics of the process and in particular a) relatively high levels of introduction of esterification catalysts (generally from 1 to 10%) and/or b) very long reaction times (generally of several tens of hours) and/or c) (very) low degrees of conversion of lactic acid (or ammonium lactate) to ethyl lactate.

Provision has also been made to prepare ethyl lactate not from lactic acid or one of its salts but from very specific compounds, such as the lactide, as disclosed in the summary of Japanese Patent No. 8-40983, or polylactides of high molecular weight (200 000), as disclosed in example 10 of U.S. Pat. No. 5,264,617.

Such processes are not economically viable since they use starting materials (lactide, polylactides) which are even more expensive than the desired product (ethyl lactate). This is because, as has already been emphasized, ethyl lactate is itself used for the purpose of the preparation of lactide and polylactides and it is economically inappropriate to wish to reconvert these products to ethyl lactate, a compound with a lower added value.

In addition, according to example 10 of U.S. Pat. No. 5,264,617, the degree of conversion of polylactide to ethyl lactate remains limited since it only achieves a value of 78%.

The result of the above is that there exists a need to have available a simple and efficient means which is less expensive than the abovementioned ones for obtaining lactic acid esters and in particular ethyl lactate, which means make it possible in particular:

- to use purified or unpurified lactic acid as starting material,
- to limit the technical and economic problems related to the presence of water in and to the removal of water from the esterification medium,
- to limit the technical and economic problems related to the use of alcohols, in particular of ethanol, in the esterification medium and to the recovery of alcohols, in particular of ethanol, from the esterification medium,
- to esterify lactic acid at relatively high temperatures in relatively short reaction times and/or without having to overdose the esterification catalysts, and
- to prepare said esters, in particular ethyl lactate, with high degrees of conversion, i.e. greater than 85%, this being achieved without employing specific, complex or expensive plant.

BRIEF DESCRIPTION OF THE INVENTION

Thus the Applicant Company has found, after much research, that such a means can consist of the conversion, before its esterification by an alcohol, of lactic acid into a specific intermediate composition which is oligomeric in nature.

DETAILED DESCRIPTION OF THE INVENTION

More specifically, a subject matter of the present invention is a process for the preparation of a lactic acid ester composition from a lactic acid composition, said process being characterized in that it comprises:

a) a stage of conversion, with removal of water, of said lactic acid composition into a lactic acid oligomeric composition exhibiting a mean degree of polymerization (MDP) of between 2 and 30 approximately, b) a subsequent stage of mixing and of reaction of said purified or unpurified oligomeric composition with an alcohol, in the presence of a transesterification catalyst, to esterify all or a portion of the lactic acid present, in a monomeric, dimeric, oligomeric or polymeric form, in said oligomeric composition, and c) an optional stage of purification of the lactic acid ester composition thus obtained.

The preliminary conversion of the lactic acid composition into an oligomeric composition as described exhibits the undeniable advantage of very substantially limiting the need for removal of water during the subsequent stage of esterification and thus of minimizing, indeed even of eliminating, the technical/economic problems related to the azeotropic distillation or pervaporation operations conventionally employed during said stage.

The term "lactic acid composition" within the meaning of the present invention is understood to mean in particular any aqueous solution of lactic acid, whatever its process of preparation and its characteristics, it being possible for said solution, for example, to exhibit a highly variable dry matter (DM) and a highly variable lactic acid purity. It can in particular be commercial solutions with a dry matter (DM) content of 50, 80, 88 or 90%, it being understood, as mentioned, for example, in U.S. Pat. No. 5,210,296 (cf. column 1, lines 50-57), that such solutions are in fact mixtures of water and of monomers, of dimers and of oligomers of lactic acid.

Such solutions can, in addition, exhibit variable levels of impurities. In consequence of which, the lactic acid composition which can be used as starting material in the context of the invention can be composed of any one of the commercially available aqueous solutions said to be of "industrial", "technical", "food" or "FCC", "pharmaceutical" or "USP" quality, including their buffered and/or heat-stabilized alternative forms. They can also be aqueous solutions which can comprise lactic acid existing, in all or in part, in the form of salt(s) capable of significantly dissociating before and/or during the esterification stage, such as ammonium lactate.

In addition, and although this does not constitute the preferred alternative form of the process according to the invention, the lactic acid composition employed may already, because of a specific preparation or recycling process, in combination or not in combination with the process according to the invention, comprise traces or several percent of lactic acid ester(s).

In accordance with the invention, said composition is converted, in a first stage, into a lactic acid oligomeric composition, this being achieved with removal of water.

This conversion is advantageously carried out by simple evaporation in one or several stages, this being carried out until a specific oligomeric composition, namely exhibiting a mean degree of polymerization (MDP) of between 2 and 30 approximately, is obtained. Such a composition exhibits the advantage, in addition to constituting a limited water supply means for the purpose of the subsequent esterification stage, of minimizing the cost of resolution of the processing problems, mixing, transportation and other unit operations, encountered with much more viscous products, such as polylactides and other polymers of high molecular weights, used as starting material in the abovementioned U.S. Pat. No. 5,264,617.

The time necessary to obtain, in particular by evaporation, the oligomeric composition depends first on the initial water content of the lactic acid composition and on the operating conditions applied during this conversion stage.

The conversion can, by way of example, be carried out at a temperature of 100 to 170° C. approximately and at atmospheric pressure or under a more or less high vacuum, generally between 20 and 500 millibar (mbar), i.e. between 2 000 and 50 000 Pascals (Pa).

Although this is in no way compulsory, this oligomerization stage can additionally advantageously be carried out in the presence of at least one transesterification catalyst for the purpose in particular of accelerating the removal of the water. One noteworthy advantage of the process according to the invention is, furthermore, to make it possible to use the same function of a means, in this instance the function of catalyst for the transesterification of a chemical compound, at two points in said process, namely during stage a) of conversion of lactic acid to oligomeric composition and then during stage b) of mixing said composition with an alcohol for the purpose of esterifying the lactic acid. This means can furthermore be identical in nature and can be present in identical amounts during these two successive stages.

In consequence of which, the process according to the invention can be characterized in that said stage a) is also carried out in the presence of a transesterification catalyst, the latter preferably being identical to the catalyst in the presence of which said stage b) is carried out.

According to another alternative form, the transesterification catalyst in the presence of which said stage b) is carried out was employed, in all or in part, during said stage a). The notion of "transesterification catalyst" is in this instance in no way limiting and should be understood as including any entity of chemical or enzymatic nature capable of advantageously catalyzing at least one of the two abovementioned stages a) and b). This notion encompasses in particular all the "esterification" or "transesterification" catalysts disclosed in one or other of the abovementioned patents and in particular column 6, lines 44-59, of U.S. Pat. No. 5,723,639, the content of which is incorporated by reference herein, and their functional equivalents. Preferably, the trans-esterification catalyst is an acid catalyst chosen in particular from the group consisting of sulfuric acid, hydrochloric acid, phosphoric acid, p-toluenesulfonic acid, methanesulfonic acid, propane-1,3-disulfonic acid, the acid salts of said acids and acid resins.

As indicated, the process according to the invention does not in any way require the use of levels of catalysts which are greater than those conventionally used. These levels generally lie between 0.01 and 10%, expressed as dry weight of catalyst with respect to the dry weight of lactic acid, in the monomeric, dimeric, oligomeric or other form, in the free or unfree form, present in the reaction medium.

According to an alternative form of the process according to the invention, the level of catalyst is less than 1%, preferably of between 0.01 and 0.9%. It can, for example, be of the order of 0.1 to 0.5% for the purpose of the preparation of ethyl lactate, these values being significantly lower than those disclosed in the abovementioned literature for such a preparation. As specified, the transesterification catalyst may or may not have been employed, and completely or not completely, from stage a) for conversion of the lactic acid composition into oligomeric composition. Characteristically, the latter exhibits a mean degree of polymerization (MDP) of 2 to 30 approximately, said MDP being calculated according to the following formula:

$$MDP = \frac{18}{\frac{[100 \times 90.08]}{T} - 72}$$

where T corresponds to the mass of lactic acid monomer (CH3-CHOH—COOH; 90.08 g/mol) present in 100 dry g of oligomeric composition. This mass is determined after saponification (20 minutes at 100° C.) by excess sodium hydroxide of a sample of the oligomeric composition of predetermined weight (0.1 to 0.3 g). After neutralization of the reaction mixture, the latter is analyzed by the High Performance Liquid Chromatography (HPLC) technique with detection by refractometry. This analysis can be carried out on a cation-exchange column of "SHODEX™ SH 1011" type using N/100 sulfuric acid as eluent. This technique makes it possible to determine the mass of lactic acid monomer present in the tested sample and, by simple calculation, the mass T present in 100 g of oligomeric composition.

Preferably, the lactic acid oligomeric composition exhibits an MDP of between 2 and 15 approximately and in particular of between 3 and 10 approximately.

These MDP values very clearly do not in any way exclude the oligomeric composition for which the preparation is claimed from being able to comprise, from the form of traces up to levels of the order of 10 to 25%, for example, compounds such as lactic acid monomer, lactide and/or lactic acid polymers exhibiting a degree of polymerization greater than the upper limit of the MDP ranges claimed. After it has been prepared, the oligomer composition can optionally be subjected to a purification treatment, in one or more stages, targeted in particular at lowering the content therein of at least one of such compounds and/or of residual water.

In accordance with the present invention, the purified or unpurified lactic acid oligomeric composition is subsequently subjected, in the presence of a catalyst, to a stage b) of mixing and of reaction with an alcohol for the purpose of esterifying all or a portion of the lactic acid present, in the monomeric, dimeric, oligomeric or polymeric form, in said composition. The alcohol employed can consist in particular of an aliphatic alcohol comprising from 1 to 6 carbon atoms, such as those disclosed in the abovementioned patents. The alcohol is preferably chosen from the group consisting of aliphatic alcohols comprising from 2 to 5 carbon atoms and more preferably still from the group consisting of ethanol, n-butanol and isobutanol. It can advantageously be ethanol, as will be exemplified below.

The alcohol is generally employed in a proportion of 1 to 10 mol per mole of lactic acid monomer present in the oligomeric composition, it being possible for the number of moles of lactic acid monomer present in said composition to be deduced from the mass calculation as described above.

The alcohol is preferably employed in a proportion of 1.5 to 5 mol per mole of lactic acid monomer.

The nature and the amounts of catalyst which can be present during this stage b) for esterification of lactic acid by an alcohol have been described above, it being remembered that any transesterification catalyst was able to be employed, in all or in part, from stage a) for producing the oligomeric composition from lactic acid.

Preferably, the temperature of the reaction medium during this stage b) is also between 100 and 170° C., including when the alcohol employed consists of ethanol.

Furthermore, the Applicant Company has found that, in the case of ethanol in particular, this temperature can advantageously be within a range from 100° C. to 145° C., i.e. within a range which makes it possible to carry out an esterification reaction efficiently in relatively short times, generally of less than 10 hours, and without the risk of racemization of the lactic acid and/or of the ester.

Furthermore, said reaction is carried out under simple "autogenous" pressure, i.e. under the vapor pressure alone of the reaction mixture at the reaction temperature.

Under these conditions, the yield of lactic acid ester is generally greater than 85%.

The lactic acid ester composition obtained on conclusion of the esterification stage b) can be used as it is, i.e. without a subsequent purification stage.

According to a first alternative form, said composition is subjected to at least one purification treatment for the purpose of removing therefrom in particular any catalyst, any free alcohol and/or any possible trace of water which it might comprise. Such a treatment can consist in particular of a simple or multiple distillation treatment.

The alcohol present in the alcoholic fraction resulting from said distillation treatment can subsequently be dehydrated, in particular by pervaporation treatment or dehydration treatment over a molecular sieve, and can then advantageously be recycled in the esterification stage b) of the process according to the invention.

By way of example, the lactic acid ester composition, for example ethyl lactate composition, recovered on conclusion of stage b) can be purified by a double distillation treatment for the purposes of removing therefrom in particular 1) ethanol and then 2) the catalyst and the traces of lactic acid and/or of ethyl lactoyllactate (esterified dimer) possibly present. The ethanolic fraction thus obtained by distillation can then be subjected to a pervaporation treatment for the purpose of dehydrating it completely and then, optionally, to a stage of recycling to the esterification stage b).

Likewise, a double distillation treatment can make it possible to obtain, inter alia, a residue comprising lactic acid, in the free and/or esterified form, and oligomers of lactic acid, in the free and/or esterified form. Such a residue can also be subjected to a stage of recycling to the esterification stage b).

The processes and plant suitable for being used for the purpose of the purification, in one or more stages, of a lactic acid ester composition obtained in accordance with the invention or of the possible recovery of the alcohol are those conventionally available to persons skilled in the art and include those disclosed in the literature, in particular in the abovementioned U.S. Pat. Nos. 5,247,059, 5,210,296 and 5,723,639, the content of which are incorporated by reference herein.

In consequence of which, there is henceforth available a novel process for the preparation of lactic acid esters which is simultaneously simple, efficient and inexpensive, it being possible for said process advantageously to be carried out continuously because, inter alia, of the good fluidity of the intermediate product which the lactic acid oligomeric composition as described constitutes, which composition is generally already liquid at temperatures of the order of 80 to 100° C. and can therefore easily be conveyed to the esterification stage b).

The process according to the invention is very particularly suited to the preparation of ethyl lactate, it being possible for this product advantageously to be used in the abovementioned fields of activity, including, as has been found by the Applicant Company, in a novel use of solvent for the preparation of gelled compositions of any nature and destination, in particular those comprising an alditol diacetal, such as dibenzylidene sorbitol (DBS) and its derivatives, in particular alkylated derivatives.

EXAMPLE 1

1 kg of a lactic acid composition consisting of an 88% aqueous lactic acid solution and 4 g of 96% concentrated sulfuric acid are introduced into a rotary evaporator. Said composition is converted by heating the reaction medium at 130° C. and under vacuum (100-1 000 mbar) for a period of 5 hours.

650 g approximately of a completely fluid lactic acid oligomeric composition are thus obtained. The mass of lactic acid monomer present in said composition and then the mean degree of polymerization (MDP) of said composition are calculated as indicated above.

In the present case, a lactic acid oligomeric composition is obtained with an MDP of 5.9 approximately.

The composition is then mixed, continuously and without an intermediate purification stage, with ethanol, in a proportion of 3 mol of ethanol per mole of lactic acid monomer present in the composition, and without addition of transesterification catalyst. After esterifying for 8 hours at 140° C. and under autogenous pressure, the resulting ethyl lactate composition is recovered. The ethyl lactate yield lies at a value significantly greater than 85%, in this instance 96%.

The ethyl lactate composition thus recovered is subsequently subjected to a purification treatment by distillation. As a consequence of which, an ethyl lactate composition exhibiting a purity of greater than 99% is obtained.

EXAMPLE 2

The advantage of the purified ethyl lactate composition obtained according to Example 1 as solvent is evaluated for the purpose of the preparation of a gel composition comprising, inter alia, 2% by weight of dibenzylidene sorbitol (DBS), 0.5% of hydroxypropyl cellulose (HPC), 40.5% of 3-methyl-3-methoxybutanol (MMB), 15% of ethanol, 2% of polyvinylpyrrolidone (PVP), 5% of water, 20% of fragrance and 5% of dimethicone copolyol (DCP). The ethyl lactate is employed in a proportion of 10% of the weight of said composition. The latter is prepared by mixing under warm conditions (≈90° C.) two intermediate compositions respectively comprising:

HPC, MMB, PVP and ethyl lactate, for one, and
DBS, ethanol and water, for the other.

After complete dissolution of the DBS in the resulting mixture, the fragrance, which had been mixed beforehand with the DCP, is incorporated therein.

After homogenization, the composition thus obtained is placed in a mold for the purpose of obtaining a gelled article of precise shape. It is found that the composition obtained exhibits good homogeneity, good transparency and good gel hardness, greater than that obtained by substituting the ethyl lactate, weight for weight, with propylene glycol or MP diol. In addition, as a result of its reduced hygroscopicity in comparison with the other solvents tested, ethyl lactate allows the gel composition to lose weight to a greater extent and more uniformly over time, which constitutes an advantageous result when said composition is intended to be used as gel for treating the surroundings.

EXAMPLE 3

1 kg of an 88% aqueous lactic acid solution is introduced into a jacketed reactor. Said solution is converted by heating the reaction medium at 150° C. and under vacuum for a period of 5 hours. 690 g approximately of a completely fluid lactic acid oligomeric composition are thus obtained. In the present case, a lactic acid oligomeric composition with an MDP of 3.4 is obtained. The latter is then mixed with ethanol (1 240 g), in a proportion of 3 mol of ethanol per mole of lactic acid monomer, and with 4 g of 96% concentrated sulfuric acid. After esterifying for 8 hours at 140° C. and under autogenous pressure, the resulting ethyl lactate composition is recovered. The yield of ethyl lactate is established to be 90%. The ethyl lactate composition thus recovered can subsequently be subjected to a purification treatment by distillation.

This example shows that stage a) in accordance with the process according to the invention can be carried out in the absence of any transesterification catalyst.

EXAMPLE 4

130 g of an ethyl lactate distillation residue composed in particular of 12% approximately of ethyl lactate, of 12% approximately of lactic acid and of oligomers of lactic acid (in the free or esterified form) is brought to reflux for 4 hours in the presence of 1.5 g of sulfuric acid and 115 g of ethanol. A composition comprising predominantly (approximately 60% by weight) ethyl lactate is thus obtained, the remainder of said composition being mainly composed of dimers of lactic acid (in the free or esterified form).

This example shows that it is possible advantageously to envisage, in the context of the invention, recycling a distillation residue comprising lactic acid oligomers to the esterification stage b).

The invention claimed is:

1. A process for the preparation of a lactic acid ester composition from a lactic acid composition, comprising:
   a) a stage of conversion, with removal of water, of said lactic acid composition into a lactic acid oligomeric composition exhibiting a mean degree of polymerization (MDP) of between 3 and 30,
   b) a subsequent stage of mixing and of reaction of said oligomeric composition which is purified or unpurified with an alcohol, in the presence of a transesterification catalyst, for the purpose of esterifying all or a portion of the lactic acid present, in a monomeric, dimeric, oligomeric or polymeric form, in said oligomeric composition, and
   c) an optional stage of purification of the lactic acid ester composition thus obtained.

2. The process as claimed in claim 1, wherein stage a), for the conversion of the lactic acid composition into an oligomeric composition, is also carried out in the presence of a transesterification catalyst.

3. The process as claimed in claim 2, wherein said catalyst is identical to the catalyst in the presence of which the esterification stage b) is carried out.

4. The process as claimed in claim 2, wherein the catalyst, in the presence of which the esterification stage b) is carried out, was employed, in all or in part, during the conversion stage a).

5. The process as claimed in claim 2, wherein said catalyst is selected from the group consisting of sulfuric acid, hydrochloric acid, phosphoric acid, p-toluenesulfonic acid, methanesulfonic acid, propane-1,3-disulfonic acid, the acid salts of said acids and acid resins.

6. The process as claimed in claim 1, wherein the level of transesterification catalyst present during the esterification stage b) and optionally during the conversion stage a) is less than 1%, this percentage being expressed as dry weight of catalyst with respect to the dry weight of lactic acid, in the monomeric, dimeric, oligomeric or other form, in the free or unfree form, present in the reaction medium.

7. The process as claimed in claim 6 wherein the level of said catalyst is of between 0.01 and 0.9%.

8. The process as claimed in claim 1, wherein the lactic acid oligomeric composition exhibits a mean degree of polymerization (MDP) of between 3 and 15.

9. The process as claimed in claim 8, wherein said lactic acid oligomeric composition exhibits a mean degree of polymerization (MDP) of between 3 and 10.

10. The process as claimed in claim 1, wherein the alcohol employed during the esterification stage b) is selected from the group consisting of aliphatic alcohols comprising from 2 to 5 carbon atoms, and wherein the temperature of the reaction medium, during said stage b), is between 100 and 170° C.

11. The process as claimed in claim 10, wherein said aliphatic alcohol is selected from the group consisting of ethanol, n-butanol and isobutanol.

12. The process as claimed in claim 10, wherein the alcohol consists of ethanol and in that the temperature of the reaction medium is between 100 and 145° C.

13. The process as claimed in claim 1, wherein the lactic acid ester composition obtained on conclusion of the esterification stage b) is subjected to at least one purification treatment.

14. The process as claimed in claim 13, wherein the purification treatment is a simple or multiple distillation treatment.

15. The process as claimed in claim 1, wherein it is carried out continuously.

16. A novel process for preparing a lactic acid ester composition, comprising:
   a) the stage of conversion, with removal of water, of said lactic acid composition into a lactic acid oligomeric composition exhibiting a mean degree of polymerization CMDP) of between 3 and 15,
   b) the subsequent stage of mixing and reacting said oligomeric composition in the reaction medium with an alcohol selected from the group consisting of aliphatic alcohols comprising from 2 to 5 carbon atoms, in the presence of a transesterification catalyst in an amount of 0.01 and 0.9%, for the purpose of esterifying all or a portion of the lactic acid present, in a monomeric, dimeric, oligomeric or polymeric form, wherein the temperature of the reaction medium is between 100 and 170° C., and
   c) the stage of purification of the lactic acid ester composition with a simple or multiple distillation treatment.

* * * * *